United States Patent [19]
Rossabi et al.

[11] Patent Number: 5,889,217
[45] Date of Patent: *Mar. 30, 1999

[54] PROCESS AND APPARATUS FOR OBTAINING SAMPLES OF LIQUID AND GAS FROM SOIL

[76] Inventors: Joseph Rossabi, 105 Michael Ct., Aiken, S.C. 29801; Christopher P. May, 5002 Hesperus Dr., Columbia, Md. 21044; Bradley E. Pemberton, 131 Glencarin Dr., Aiken, S.C. 29803; Jim Shinn, Box 65, RFD. #1, South Royalton, Vt. 05068; Keith Sprague, Box 234 Rte. 14, Brookfield, Vt. 05036

[*] Notice: This patent issued on a continued prosecution application filed under 37 CFR 1.53(d), and is subject to the twenty year patent term provisions of 35 U.S.C. 154(a)(2).

[21] Appl. No.: 650,473

[22] Filed: May 20, 1996

Related U.S. Application Data

[63] Continuation-in-part of Ser. No. 645,443, May 13, 1996, abandoned.

[51] Int. Cl.$^6$ .................................................... E21B 43/00
[52] U.S. Cl. ................................................... 73/864.74
[58] Field of Search .................. 73/863.23–863.25, 73/864.34, 864.73, 864.74; 166/264; 175/58–60

[56] References Cited

U.S. PATENT DOCUMENTS

| | | |
|---|---|---|
| 2,210,546 | 8/1940 | Hassler .................................. 73/864.74 |
| 2,214,551 | 9/1940 | Edwards . |
| 3,722,589 | 3/1973 | Smith et al. . |
| 3,930,754 | 1/1976 | Mogg et al. . |
| 4,160,622 | 7/1979 | Colburn . |
| 4,745,801 | 5/1988 | Luzier .................................. 73/863.24 |
| 4,759,227 | 7/1988 | Timmons . |
| 4,807,707 | 2/1989 | Handley et al. ......................... 175/59 |
| 5,010,776 | 4/1991 | Lucero et al. . |
| 5,035,149 | 7/1991 | Wierenga . |

FOREIGN PATENT DOCUMENTS 0076994  1/1954  Denmark ............................ 73/864.74

OTHER PUBLICATIONS

Harrison et al., "A Probe Method for Soil Water Sampling and Subsurface Measurements" Water Resources Research, vol. 17, No. 6, pp. 1731–1736, Dec. 1981.

*Primary Examiner*—Robert Raevis
*Attorney, Agent, or Firm*—Hardaway Law Firm P.A.

[57] ABSTRACT

An apparatus and process for obtaining samples of liquid and gas from subsurface soil is provided having filter zone adjacent an external expander ring. The expander ring creates a void within the soil substrate which encourages the accumulation of soil-borne fluids. The fluids migrate along a pressure gradient through a plurality of filters before entering a first chamber. A one-way valve regulates the flow of fluid into a second chamber in further communication with a collection tube through which samples are collected at the surface. A second one-way valve having a reverse flow provides additional communication between the chambers for the pressurized cleaning and back-flushing of the apparatus.

11 Claims, 4 Drawing Sheets

PROCESS AND APPARATUS FOR OBTAINING SAMPLES OF LIQUID AND GAS FROM SOIL

RELATED APPLICATIONS

This application is a continuation-in-part of U.S. patent application Ser. No. 08/645,443 having an attorney docket number SRS-94,0035, filed May 13, 1996, and incorporated herein by reference, now abandoned.

This application relates generally to subsurface sampling devices, and more particularly to an apparatus and process for obtaining liquid and gas samples from subsurface soil. The United States Government has rights in this invention pursuant to Contract No. DE-AC09-89R18035 between the U.S. Department of Energy (D.O.E.) and Westinghouse Savannah River Company.

BACKGROUND OF THE INVENTION

Contamination of subsurface soil and its environmental impact has been the subject of considerable public attention and has caused much concern with respect to the storage and disposal of materials such as waste with the potential for contamination. When exposed to soil, it is common for such contaminating or hazardous materials to lodge in the interstices or pore space of the soil, or to become part of the soil solutions, which can be generally defined as the interstitial water in the soil together with solutes and dissolved gases. The frequent lack of detectability by sight of such hazardous materials and subsurface soil solutions can mean that the problems caused by such hazardous materials often do not manifest themselves until the situation has reached a critical point. The need exists, therefore, for methods and apparatuses for obtaining samples of liquid and gas from subsurface soil in order to subsequently analyze some samples for the possible presence of hazardous materials. Even where no concern for hazardous materials exists, it is important to be able to obtain samples of liquid and gas from subsurface soil for various other scientific purposes.

Various devices exist within the prior art pertaining to sampling of subsurface soil. Some such devices are for in situ collection of representative soil solution samples, and these are sometimes called lysimeters. One type of lysimeter is referred to as a suction lysimeter and utilizes a receptacle implanted in the earth having a conduit extending from the receptacle to the earth's surface and utilizing a vacuum pull through the conduit to draw soil solution samples through a filter into the receptacle and through the conduit to the earth's surface.

U.S. Pat. No. 4,759,227 to Timmons teaches an apparatus and process disclosing a lysimeter utilizing a filter section which is a rigid, porous, fluoroplastic through which moisture from soil surrounding the lysimeter can pass into a chamber of the lysimeter.

U.S. Pat. No. 5,035,149 to Wierenga discloses a soil solution sampler of the lysimeter type wherein the sampler comprises a receptacle comprised of a first tube formed from porous stainless steel to permit flow of solution through its walls, and a second tube formed of non-porous stainless steel joins to the end of the first tube. An air conduit for applying a vacuum to the interior of the receptacle and for applying positive pressure to the interior of the receptacle is provided and extends into the receptacle into the earth's surface. The sampler has a sample transfer conduit for conveying samples from the receptacle to the surface.

U.S. Pat. No. 3,930,754 to Mogg et al. discloses a portable water sampling apparatus for sampling water from a well wherein the apparatus comprises a wheeled hose reel cart which supports a long length of plastic hose or tubing with the tubing having a small diameter length of inner tubing telescoped inside itself throughout most of its length. The inner tubing passes through the wall of the outer tubing near the upper end thereof and is connected to a pressurized cylinder of gas. Admission of gas to the inner tube at its upper end when the lower ends of the tube are submerged beneath the water level in a well will force water up through an annular space between the tubes and out the upper end of the outer tube for collection. The channeled plug at the bottom of the tubes is used to prevent the tubes from collapsing and help maintain the tubes straight and together as they are lowered into the well. The channeled plug also provides a partial support for a weight to hang from the bottom of the tubes for aid in placement.

U.S. Pat. No. 4,160,622 to Colburn also discloses a portable water sampling apparatus for sampling water in a well. The apparatus of Colburn comprises a wheeled hose reel cart supporting a long length of coextruded plastic hose or tubing with the coextrusion comprising a small diameter portion of tubing attached by a web to a large diameter portion of tubing and with the small diameter tubing being connected to a pressurized cylinder of gas. A generally j-shaped piece of metal tubing is utilized and projects from the inside of the smaller tubing, which it fictionally engages, into the center of the larger tubing at the lower end thereof. When the lower ends of the tubes are well submerged beneath the water level in a well, admission of gas to the smaller tube at its upper end forces water entering the larger tubing in the annular space surrounding the metal tubing up through the larger tube and out the upper end of the larger tube for collection.

U.S. Pat. No. 3,722,589 to Smith et al. discloses a method for performing production testing of wells comprising the steps of introducing into and withdrawing from a well a small diameter tubing by an injector apparatus. While in the well, the small diameter tubing is hung in the well with its lower end adjacent a formation to be tested, and gas is injected through the tubing to lift a layer of uncontaminated reservoir fluid to the surface continued gas injection accomplishes formation flow characteristic evaluation.

U.S. Pat. No. 5,010,776 to Lucero et al. discloses an environmental contamination detection and analyzing system and method. The method and system for detecting environmental contamination according to Lucero et al. utilizes a test probe located in a medium wherein the probe is adapted to collect a fluid sample from the medium for determining the presence of a contaminant having a vapor pressure. Pneumatic communication lines extend from a test point and connect to the probe and a detector/analyzer is connected to the distal end of the communication lines of the probe. A fluid sample is taken into the probe and transported in the pneumatic communication lines by a carrier gas to the detector/analyzer for analysis of the contaminant.

Another method and apparatus for obtaining samples from the earth is disclosed in U.S. Pat. No. 2,214,551 to Edwards.

Despite the prior art references, there exists room for improvement in the art.

SUMMARY OF THE INVENTION

It is therefore an object of this invention to provide an improved apparatus and process for obtaining samples of liquid and gas from subsurface soil.

It is another object of this invention to provide a process and apparatus for obtaining samples of liquid and gas from subsurface soil which is simple and versatile to use.

It is another object of this invention to provide an apparatus and process for obtaining samples of liquid and gas from subsurface soil which can be used in a well or during cone penetrometer pushes to obtain multiple gas and liquid samples.

It is a further object of this invention to provide an apparatus and process for obtaining samples of liquid and gas from subsurface soil which can be remotely controlled.

It is a further object of this invention to provide an apparatus and process for obtaining liquid and gas samples from subsurface soil which can be used for continuous sampling.

It is a still further object of this invention to provide an apparatus and process for obtaining samples of liquid and gas from subsurface soil wherein such samples can be obtained while below the ground surface and transported to the ground surface without having to return the apparatus itself to the surface.

These as well as other objects are accomplished by an apparatus for obtaining samples of liquid and gas from soil comprising:

a cylindrical shell defining a hollow interior with a first inner diameter and a second inner diameter, the second diameter greater than the first;

an expander ring carried by an exterior of the shell;

a filter zone, defined by the outer shell and further defining at least one opening through the filter zone in communication with the hollow interior;

a first filter carried adjacent to an exterior of the filter zone and in communication with the filter zone opening;

a second filter carried along an exterior of the first filter, the second filter being in communication with the first filter having an exterior surface substantially flush with an exterior of the cylindrical shell;

a collection assembly carried within the hollow interior, the collection assembly further defining a conduit, the conduit defining a plurality of rings, each ring further defining a first flat surface and a second flat surface with each ring being traversed by the conduit;

the plurality of rings further defining a terminal first ring and a second ring a spaced distance from the first ring, the first and second rings each having an outer circumference slightly less than the first inner diameter of the cylindrical shell;

a third ring adjacent to the second ring, the third ring having an outer circumference greater than the second ring;

a terminal fourth ring, at an opposite end of the conduit from the first ring, the fourth ring having an outer circumference substantially similar to the third ring;

a first check valve housed within a first bore, the bore traversing both the second and the third ring;

a second check valve defined within a second bore, the second bore traversing both the second and the third ring;

a first tubing traversing the fourth ring, the tubing having a first end opposite the first check valve bore and a second free end;

a second tubing in communication with a bore defined between the inner and outer surface of the fourth ring, a first end of the second tubing in communication with the bore and the second end of the second tubing traversing the outer flat surface of the fourth ring;

a cylindrical tube having a first and a second open end, a first end of the tube engaging an outer circumference of the third ring in a fluid tight seal and a second end of the tube engaging the fourth ring in a fluid tight seal, thereby defining a collection chamber within an interior space of the sealed cylindrical tube;

wherein, when the first and the second rings are positioned within the cylindrical shell, the first and the second rings are seated in a sealed fashion in proximity to the filter zone, permitting soil associated fluids to pass through the filter zone and into the first inner diameter of the cylindrical shell, the fluid accumulating within a space defined between the first and the second rings and flowing through the first check valve into the collection chamber wherein the fluid can be withdrawn from the collection chamber through the first tubing.

DETAILED DESCRIPTION

A sampler apparatus 1 is provided which comprises an outer metal jacket or shell 3, the interior of which defines a plurality of interconnected chambers and tubing for the collection of water, air, or other fluid samples and sample combinations from soil. As used within this specification, the terms "upper" and "lower" are in reference to the vertical orientation of the apparatus 1 as seen in FIGS. 1 and 2.

Figure 1:
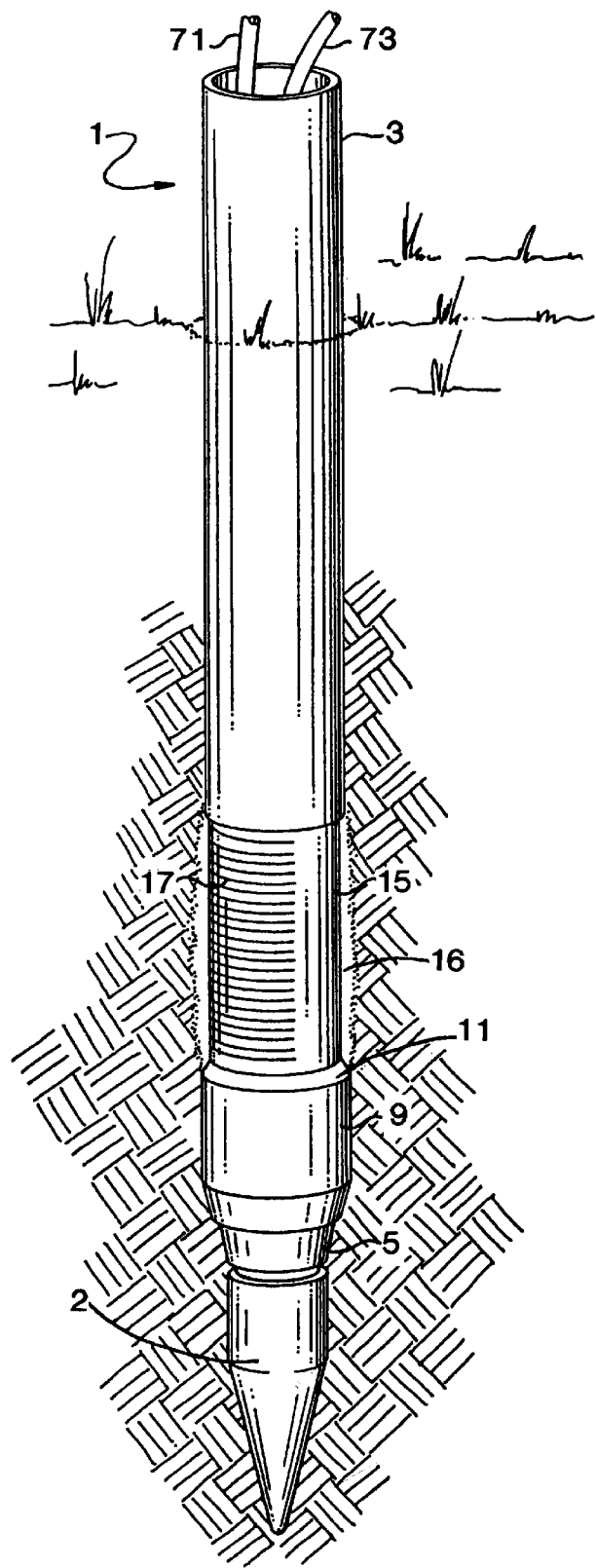
FIG. 1 is a perspective view of a preferred embodiment of this invention in relation to the subsurface environment.
Figure 2:
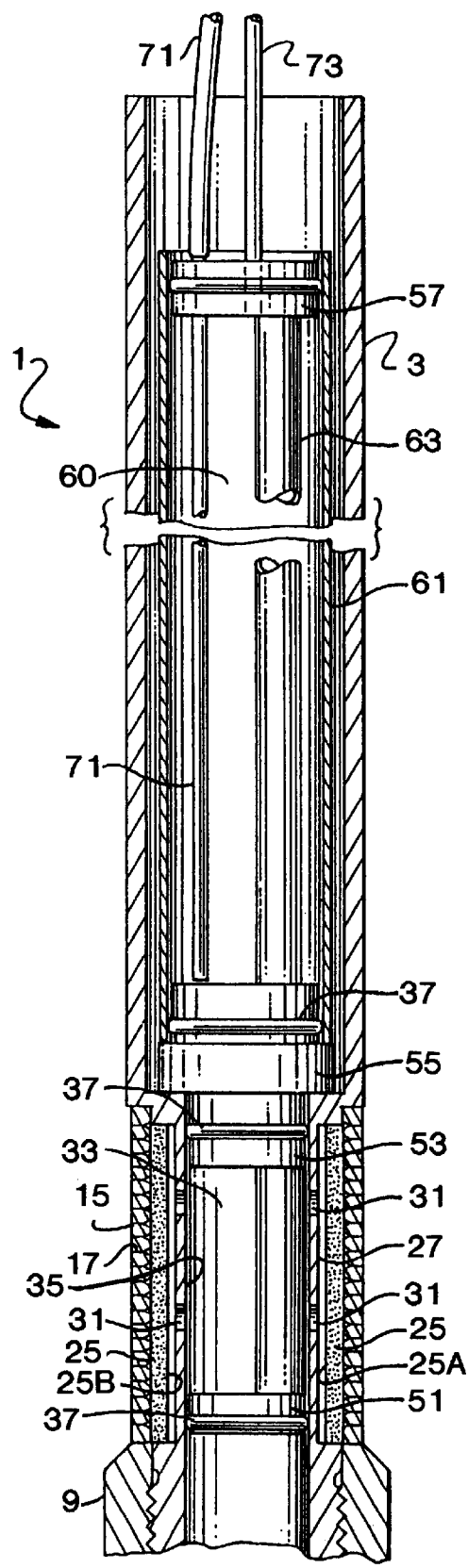
FIG. 2 is an elevational sectional view of a preferred embodiment of this invention.
Figure 3:
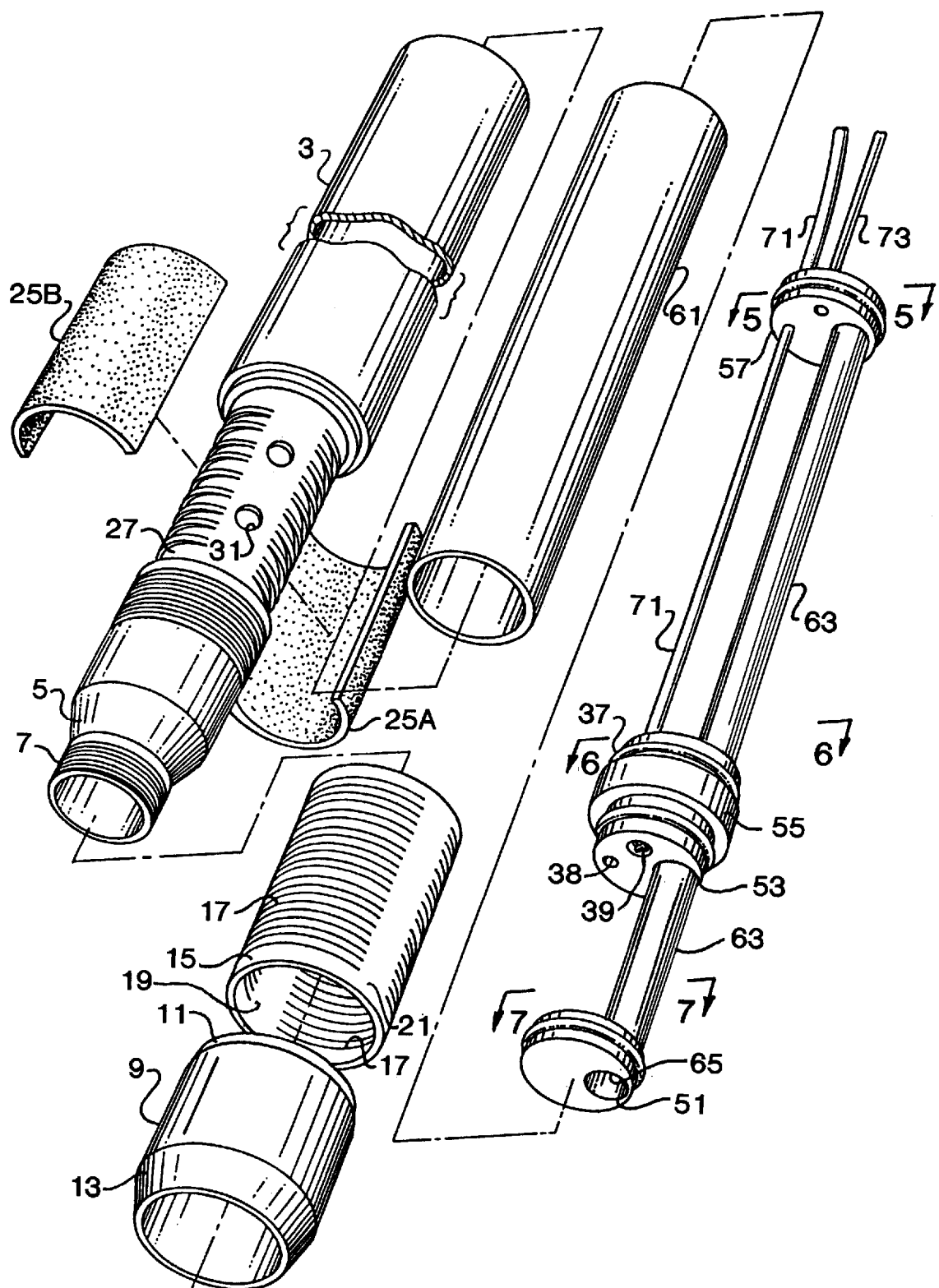
FIG. 3 is an exploded perspective view of the embodiment seen in FIGS. 1 and 2.
Figure 4:
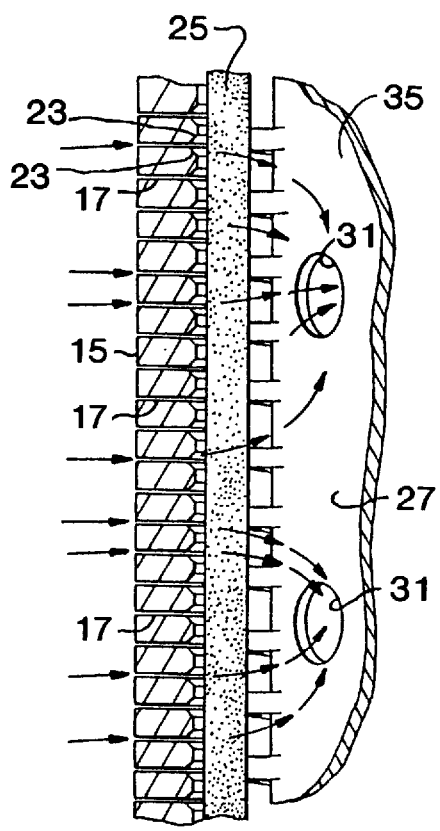
FIG. 4 is an enlarged sectional view through a filter region of the preferred embodiment of the invention.
Figure 5:
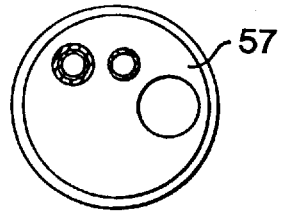
FIG. 5 is a cross section taken along line 5—5 of FIG. 3.
Figure 6:
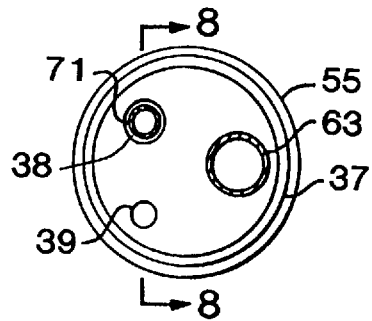
FIG. 6 is a cross section taken along line 6—6 of FIG. 3.
Figure 7:
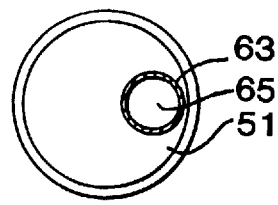
FIG. 7 is a cross section taken along line 7—7 of FIG. 3.

As best seen in reference to FIGS. 1 and 3, a lower end 5 of sampler 1 is tapered, terminating in a threaded nose 7 for connection to a conventional cone rod 2. A metal expander ring 9 is threadably attached to the shell, the ring having a complimentary tapered shape to that of the sampler. The expander ring also defines rounded edges on the upper 11 and lower 13 ring surfaces to facilitate the insertion and withdrawal of the expander ring in the soil. Adjacent the expander ring is a filter 15 comprising an outer spherical metal filter in the form of a sleeve defining a plurality of 10mm slits 17 which permit communication between the inner 19 and outer 21 surfaces of the filter sleeve. As best seen in reference to FIG. 4, the inner margins 23 of each slit are grooved to provide a beveled or chamfered inner surface, similar to grooves employed on well screens. The beveled inner groove margins facilitates the passage of fluids through the filter sleeve. The inner filter sleeve surface is in further communication with a second filter 25. In a preferred embodiment of the present invention, the second filter 25 is provided by a sintered metal having an average pore size of approximately 100 um. As seen in FIG. 3, the second filter is provided by two semicircular portions 25A and 25B which surround a recessed portion 27 of the shell exterior. When assembled, the second filter 25 and filter sleeve 15 all nest within the recessed portion 27 of the shell so that the resulting filter zone surface is substantially flush with the adjacent portions of the outer shell.

When inserted into the soil as part of a cone rod assembly, the expander ring temporarily compresses the soil adjacent the ring. As a result, a soil void 16 (FIG. 1) is provided in proximity to the filter zone which allows fluids to accumulate within the soil void. The fluid is then free to pass through the first and second filter as best seen by the directional arrows in reference to FIG. 4. The fluid enters the interior of the shell through a plurality of apertures 31 defined by the recessed portion of the shell as best seen in FIG. 2.

The fluid enters into a first receptacle 33 defined in part by an interior wall 35 of the recessed portion 27 of the shell. A lower and an upper seal of the receptacle is provided by a respective first ring 51 and a second ring 53, each said ring defining a circumferential edge carrying an O-ring 37 which engages the inner surface of the reduced diameter interior wall 35 of the shell.

Figure 8:
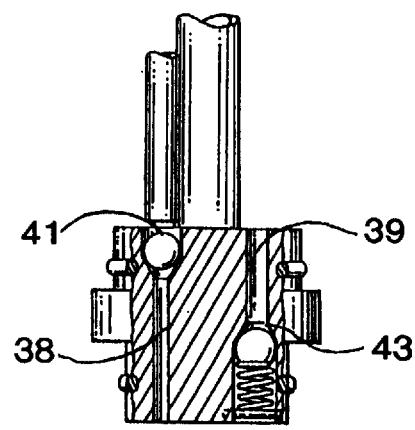
FIG. 8 is a sectional view taken along line 8—8 of FIG. 6.

Integral to second ring 53 is an upper third ring 55, ring 55 having a larger diameter than ring 53. The integral ring 53 and ring 55 seals further define a first bore 38 and a second bore 39, both of which are in communication with the lower surface of ring 53 and the upper surface of ring 55. As best seen in FIG. 8, the first bore further defines a first check valve 41 which is a low cracking pressure valve. This valve provides a one-way communication from the lower receptacle through the first bore. The second bore 39 defines a second check valve 43 which requires a relatively greater cracking pressure to open than that required in the first valve. The second valve provides one-way communication into the lower receptacle 33, opposite the flow direction of the first valve. While the illustrated valves are spring-tensioned ball valves, a variety of well known valve structures could be used, including solenoid valves.

A spaced distance above the third ring 55, a fourth ring 57 is provided having similar dimensions to that provided by ring 3. A second receptacle 60 is defined between ring 55 and ring 57 within the interior wall of a metal sleeve 61.

The metal sleeve 61 has an outer diameter slightly less than the inner diameter of the adjacent shell 3. This permits the sleeve 61 and associated receptacle 60 to reside within the interior of the shell. A collection tube 71 extends through the fourth ring 57 in a fluid-tight manner and has a first open end in close proximity to first bore 38 of ring 55. The second end of the collection tube extends beyond the upper surface of the fourth ring 57. A second tube 73 provides separate communication to the receptacle through ring 57. As seen in FIG. 3, the second tube has a first end substantially flush with a lower surface of ring 57. The second end extends beyond the upper surface of ring 57.

A common conduit 63 defining a bore 65 is provided through and between the plurality of rings. Conduit 63 maintains the integrity of each ring seal and associated receptacles and provides a pathway for multipurpose cables or fiber optics which may connect with sensors or other instrumentation typically carried within the cone portion of the penetrometer. In the illustrated embodiment, bore 65 terminates flush with the respective upper surface of ring 57 and the lower surface of ring 51.

The first tube 71 is used to collect samples from the second receptacle for transport to the surface. Where depth permits, collection through the tube is controlled by pulling a vacuum. Where vacuum pressure is insufficient, pressure can be supplied through tube 73. Also in communication with receptacle 60, to force the sample through tube 71. Once collected, the internal chambers and conduits of the collection apparatus can be cleaned and purged by applying fluid at a pressure greater than the cracking value of the second valve. The back-flushing also helps to clean and unclog the filters and fluid migration pathways. For instance, pressurized water or nitrogen gas will purge and back-flush the entire system including the upper and lower receptacle and collection tubes. Once clean, the assembly can be placed in the next collection zone and a fresh sample taken.

The present apparatus provides an improved collection assembly apparatus for carrying out the process as disclosed in the above-referenced parent application. An advantage of the present collection apparatus is that the expander ring pushes aside or compresses the soil as the collection apparatus is pushed through the soil. As a result, a slight void or headspace is created immediately behind the expander ring and in proximity to the filter zone. The void area 16 allows fluids to accumulate adjacent the filter so that filtered fluids can then enter the first receptacle. A gradient of fluid flow from the soil to the interconnected receptacles may be maintained by a vacuum applied along collection tubing 71 and tubing 73. In accordance with this invention, it has been found that the expander ring and resulting headspace defined adjacent the filter region reduces a typical collection time of one hour to just a matter of minutes.

It is also envisioned that a second expander ring (not illustrated)-similar to expander ring 9 may be carried above the filter zone by shell 3. The second expander ring will provide a barrier against seepage from above of fluid along the sides of the bore hole wall and into the desired collection area. An additional expander ring has not been found necessary but may be applicable for certain soil types or subsurface conditions.

As fluids accumulate within the first receptacle, the fluid passes through the first low-cracking pressure valve and permit the filtered fluids to enter into the second receptacle as well as tubing 71. Once the second receptacle is filled, the fluids are withdrawn along the first collection tube 73 in response to a vacuum pressure and by the simultaneous application of a pressurized (inert gas) to tube 73.

The second tube allows an inert gas, liquid, or other fluid to be supplied to the second receptacle to back-flush the entire assembly. The pressurized fluid from line 73 forces the sample into line 71. The resulting combination of pressure along with the vacuum applied to line 71, forces the sample through line 71 into the above ground surface for collection and analysis. As seen in FIG. 2, the first collection tube provides an open end in close proximity to the upper surface of the third ring as well as in close proximity to the bore 38 which houses the low cracking valve. This arrangement helps in collecting the full volume of any sample which resides in the second receptacle.

Once the sample is collected, tube 73 can be used to flush and clean the apparatus by applying a suitable fluid under sufficient pressure to valve 43, passing the cleaning fluid to the lower receptacle and through the filter to back-flush the entire assembly. Once cleaned, the collection assembly can then be positioned to a second collection depth and an additional sample taken.

While the descriptions provided above refer to gas or liquid samples being obtained separately, it is envisioned that a combination of gas and liquid sample can be obtained. More typically, however, as the apparatus according to this invention passes down into the earth, layers of materials are encountered such that the apparatus can be maintained at, for example, the layer of the water table to obtain a sample of liquid therefrom.

It is therefore seen that an improved apparatus and process for obtaining samples of liquid and gas from subsurface soil is provided. It is also seen that the process and apparatus according to this invention is simple, versatile to use and can be used in a well or during cone penetrometer pushes to obtain multiple gas and liquid samples without the need for withdrawal of the equipment to collect the samples. It is further seen that the apparatus and process of this invention can be used for continuous sampling of subsurface soil. Many variations will be apparent to those of skill in the art and such variations are embodied within the spirit and scope of the following appended claims.

That which is claimed:

1. A cone penetrometer comprising:

a cylindrical shell defining a hollow interior with a first inner diameter and a second inner diameter, said second diameter greater than said first;

an expander ring carried by an exterior of said shell;

a filter zone, defined by said shell and further defining at least one opening through said filter zone in communication with said hollow interior;

a first filter carried adjacent to an exterior of said filter zone and in communication with said filter zone opening;

a second filter carried along an exterior of said first filter, said second filter being in communication with said first filter and having an exterior surface substantially flush with an exterior of said cylindrical shell;

a collection assembly carried within said hollow interior, said collection assembly further defining a conduit, said conduit defining a plurality of rings, each said ring further defining a first flat surface and a second flat surface with each said ring being traversed by said conduit;

said plurality of rings further defining a terminal first ring and a second ring a spaced distance from said first ring, said first and said second ring having an outer circumference slightly less than said first inner diameter of said cylindrical shell;

a third ring adjacent to said second ring, said third ring having an outer circumference greater than said second ring;

a terminal fourth ring, at an opposite end of said conduit from said first ring, said fourth ring having an outer circumference substantially similar to said third ring;

a first check valve housed within a first bore, said bore traversing both said second and said third ring;

a second check valve defined within a second bore, said second bore traversing both said second and said third ring;

a first tubing traversing said fourth ring, said tubing having a first end opposite said first check valve bore and a second free end;

a second tubing in communication with a bore defined between said inner and said outer surface of said fourth ring, a first end of said second tubing in communication with said bore and said second end of said second tubing traversing said outer flat surface of said fourth ring;

a cylindrical tube having a first and a second open end, a first end of said tube engaging an outer circumference of said third ring in a fluid tight seal and a second end of said tube engaging said fourth ring in a fluid tight seal, thereby defining a collection chamber within an interior space of said sealed cylindrical tube;

wherein, when said first and said second rings are positioned within said cylindrical shell, said first and said second rings are seated in a sealed fashion in proximity to said filter zone, permitting soil associated fluids to pass through said filter zone and into said first inner diameter of said cylindrical shell, said fluid accumulating within a space defined between said first and said second rings and flowing through said first check valve into said collection chamber wherein said fluid can be withdrawn from said collection chamber through said first tubing.

2. A sampling apparatus comprising:

a tubular shaft defining an interior cylindrical chamber, said chamber further defining a first inner diameter and a second inner diameter, said first diameter less than said second diameter;

an exterior wall of said shaft defining an aperture and in communication with a portion of said chamber associated with said first inner diameter;

a filter, carried along an exterior of said shaft and in communication with said shaft aperture;

a first seal positioned in proximity to a lower terminus of said shaft and within said first inner diameter of said shaft;

a second seal positioned above said first seal and above said aperture and within said first inner diameter of said shaft, said first and said second seal thereby forming a first receptacle within said shaft for receiving filtered fluids from an exterior of said shaft;

a third seal integral to and carried above said second seal, said third seal defining a diameter greater than said second seal, said second and third seal collectively defining a first bore traversing said second and third seal and a second bore traversing said second and third seal;

a first check valve in communication with said first bore;

a second check valve in communication with said second bore;

a fourth seal carried above said third seal, said third and fourth seal forming a second receptacle between a first end and a second end of a tubular sleeve, said sleeve residing within said second inner diameter portion of said shaft;

a hollow arm carrying each said first, second, third, and fourth seal, said arm providing a fluid-tight passage through each said seal;

a withdrawal tube traversing said fourth ring and having a first end opposite said first check valve and a second free end directed away from said fourth seal;

a second tubing in communication with a bore defined between an inner and an outer surface of said fourth seal, a first end of said second tubing in communication with said bore and a second end of said tubing carried away from said fourth seal.

3. A collection apparatus comprising:

an outer housing, said housing defining a first receptacle, said first receptacle in fluid communication with a second receptacle carried within said housing, said first and said second receptacle further defining a common opening, said opening defining a valve;

a filter, carried by said housing, and in communication with said first receptacle by an aperture defined by said housing;

a first tube in communication with said second receptacle;

a second tube in communication with said second receptacle;

an expander ring carried by an exterior of said housing and in proximity to said filter;

wherein, when said collection apparatus is inserted into a soil, said expander ring creates a void adjacent said filter in which fluids accumulate, said fluids further migrating through said filter and entering said first receptacle, passing through said common opening and said valve and entering said second receptacle, said fluids being withdrawn through said first tubing to a surface of said soil.

4. A process of collecting a subsurface fluid sample comprising:

pushing a collection apparatus to a desired depth;

creating a head space adjacent a filter region of said apparatus;

establishing a gradient flow of fluid from an exterior of said apparatus to an interior of said apparatus, said gradient flow passing through said filter region;

passing said sample into a first receptacle;

transferring said sample through a first check valve into a second sealed receptacle;

applying a positive pressure to said second receptacle, said positive pressure forcing said sample through a collection line for retrieving said sample at said desired depth, said collection line in communication with an above-ground surface.

5. The process according to claim 4 comprising the additional steps of:

pushing said collection apparatus to a second desired depth;

collecting a sample from said second depth.

6. The process according to claim 4 comprising the additional steps of:

blocking said collection line;

applying a pressurized fluid to said second receptacle;

passing said pressurized fluid through a second check valve and into said first sealed receptacle;

back-flushing said filter zone by the continued application of said pressurized fluid.

7. A collection apparatus comprising:

a first lower receptacle;

an upper receptacle having an outer wall, said upper receptacle in selective communication with said lower receptacle through at least one valve;

a filter carried by an exterior of said lower receptacle, said filter in communication with said lower receptacle through an aperture defined by a surface of said receptacle;

an expander ring carried by an outer housing of said apparatus and positioned in proximity to said filter;

a collection means for collecting a fluid sample from said upper receptacle; and a cylindrical tube carried within said housing and defining said outer wall of said upper receptacle.

8. The apparatus according to claim 7 wherein an inner wall of a housing defines an outer wall of said upper receptacle.

9. The apparatus according to claim 7 wherein said apparatus is adapted for attachment to a cone rod.

10. The apparatus according to claim 7 wherein said apparatus further defines a hollow conduit extending a length of said apparatus, said conduit traversing said upper and said lower receptacle in a fluid-tight manner.

11. The apparatus according to claim 7 wherein said collection means further defines a first tube in communication with said upper receptacle for removal of a sample and a second tube for supplying a pressurized fluid to said upper receptacle.

* * * * *

UNITED STATES PATENT AND TRADEMARK OFFICE
Certificate

Patent No. 5,889,217                                                                       Patented: March 30, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Joseph Rossabi, Aiken, SC; Christopher P. May, Columbia, MD; Bradley E. Pemberton, Aiken, SC; Jim Shinn, South Royalton, VT; Keith Sprague, Brookfield, VT; and Brian D. Riha, Augusta, GA.

Signed and Sealed this Fourth Day of June 2002.

HEZRON E. WILLIAMS
*Supervisory Patent Examiner*
Art Unit 2856